(12) United States Patent
Ying et al.

(10) Patent No.: US 7,919,422 B2
(45) Date of Patent: Apr. 5, 2011

(54) CHIRAL BISOXAZOLINE CATALYSTS

(75) Inventors: Jackie Y Ying, The Nanos (SG); Su Seong Lee, The Nanos (SG); Sukandar Hadinoto, The Nanos (SG)

(73) Assignee: Agency for Science, Technology and Research, Sydney (AU)

( * ) Notice: Subject to any disclaimer, the term of this patent is extended or adjusted under 35 U.S.C. 154(b) by 481 days.

(21) Appl. No.: 11/885,984

(22) PCT Filed: Mar. 8, 2005

(86) PCT No.: PCT/SG2005/000072
§ 371 (c)(1),
(2), (4) Date: Oct. 10, 2008

(87) PCT Pub. No.: WO2006/096131
PCT Pub. Date: Sep. 14, 2006

(65) Prior Publication Data
US 2011/0034700 A1    Feb. 10, 2011

(51) Int. Cl.
C07D 413/06 (2006.01)
B01J 32/00 (2006.01)
C07F 7/08 (2006.01)
C07F 7/10 (2006.01)

(52) U.S. Cl. ............................ 502/150; 548/101

(58) Field of Classification Search .................. None
See application file for complete search history.

(56) References Cited

FOREIGN PATENT DOCUMENTS
FR 2826298 A1 12/2002
WO 03018191 A1 3/2003
WO 03039746 A1 5/2003

OTHER PUBLICATIONS

International Search Report for counterpart PCT/SG2005/000072 (4 pages).
Weissberg, A et al, "Unprecedented preparation of pincer bis(oxazolinyl)phenyl ligands on solid support and their use in the first heterogeneously-catalyzed enantioselective allylation of aldehydes", Chemical Communications (2003), vol. 13, pp. 1538-1539.
Corma, A et al, "Chiral copper(II) bisoxazoline covalently anchored to silica and mesoporous MCM-41 as a heterogeneous catalyst for the enantioselective Friedel-Crafts hydroxyalkylation", Chemical Communications (2002), vol. 10, pp. 1058-1059.
Park, JK et al, "Heterogeneous asymmetric Diels-Alder reactions using a copper-chiral bis(oxazoline) complex immobilized on mesoporous silica", Tetrahedron: Asymmetry (2001), vol. 12, No. 21, pp. 2931-2935.
Orlandi, S et al, "An insoluble polymer-bound bis-oxazoline copper(II) complex: a highly efficient heterogeneous catalyst for the enantioselective Mukaiyama aldol reaction", Angewandte Chemie, International Edition (2001), vol. 40, No. 13, pp. 2519-2521.
Burguete, MI et al, "Bis(oxazoline)copper complexes covalently bonded to insoluble support as catalysts in cyclopropanation reactions", Journal of Organic Chemistry (2001), vol. 66, No. 26, pp. 8893-8901.
Johnson JS et al, "Chiral Bis(oxazoline) Copper (II) Complexes: Versatile Catalysts for Enantioselective Cycloaddition, Aldol, Michael, and Carbonyl Ene Reactions", Acc. Chem. Res. 2000, 33, 325-335.
Clarke, RJ et al, "Mesopore immobilised copper bis(oxazoline) complexes for enantioselective catalysis", Chem. Comm. 2001, 1936-1937.
Fache, F et al "Nitrogen-Containing Ligands for Asymmetric Homogeneous and Heterogeneous Catalysis", Chem. Rev. 2000, 100, 2159-2231.
Rechavi, D et al "Enantioselective Catalysis Using Heterogeneous Bis(oxazoline) Ligands: Which Factors Influence the Enantioselectivity?", Chem. Rev. 2002, 102, 3467-3493.
Annunziata, R et al "Poly(ethylene glycol)-Supported Bisoxazolines as Ligands for Catalytic Enantioselective Synthesis", J. Org. Chem. 2001, 66, 3160-3166.
Rechavi, D et al "Heterogenization of a Chiral Bis(oxazoline) Catalyst by Grafting onto Silica", Organic Letters, 2001 Am. Chem. Soc. vol. 3, No. 16, 2493-2496.
Ghosh, AK et al "C2-Symmetric Chiral bis(oxazoline)-metal complexes in catalytic asymmetric synthesis", Tetrahedron: Asymmetry 9 (1988), 1-45.
Pfaltz, A "From Corrin Chemistry to Asymmetric Catalysis—A Personal Account", Synlett 1999, No. S1, 835-842.
Evans, DA et al "A New Copper Acetate-Bis(oxaline)-Catalyzed, Enantioselective Henry Reaction", J. Am. Chem. Soc. 2003, 125, 12692-12693.
Palomo, C et al "Catalytic Enantioselective Conjugate addition of Carbamates", J. Am. Chem. Soc. 2004, 126, 9188-9189.
International Preliminary Report on Patentability for counterpart PCT/SG2005/000072 (8 pages).

*Primary Examiner* — Kamal A Saeed
(74) *Attorney, Agent, or Firm* — Wood, Herron & Evans, LLP

(57) ABSTRACT

The present invention describes a heterogeneous chiral catalyst comprising a heterogeneous chiral catalyst precursor complexed with a metal species. The precursor comprises a chiral bisoxazoline group coupled to an inorganic substrate. The heterogeneous chiral catalyst may be capable of catalysing a chemical reaction, for example cyclopropanation, and the chemical reaction may be capable of generating a chiral product.

45 Claims, 1 Drawing Sheet

(a) (S)-tert-leucinol, 90°C (b) p-toluenesulfonic chloride, triethylamine, DMAP, $CH_2Cl_2$, RT (a) Step 1: MeLi. Step 2: 3-iodopropyltrimethoxysilane.

(b) HMDS.

(c) Toluene, 90°C.

CHIRAL BISOXAZOLINE CATALYSTS

TECHNICAL FIELD

The present invention provides a heterogeneous chiral bisoxazoline catalyst, and a process for making it.

BACKGROUND OF THE INVENTION

Chiral bisoxazolines are among the most useful catalysts in asymmetric organic reactions. Heterogeneous catalysts are desirable as they provide for easier, faster and more efficient separation and recovery of the catalyst. Consequently a great deal of research has been done to heterogenize chiral bisoxazolines. While most heterogenized bisoxazolines involve the use of polymer supports, a number of silica-supported bisoxazoline catalysts have been developed. These silica-supported bisoxazolines typically show lower enantioselectivities and reactivities than their homogeneous counterparts.

There is therefore a need for a bisoxazoline catalyst that provides for easy separation of the catalyst from products and provides good enantioselectivity and reactivity.

OBJECT OF THE INVENTION

It is an object of the present invention to overcome or substantially ameliorate at least one of the above disadvantages. It is a further object to at least partially satisfy the above need.

SUMMARY OF THE INVENTION

According to a first aspect of the invention there is provided a heterogeneous chiral catalyst precursor comprising a chiral bisoxazoline group coupled to an inorganic substrate.

The chiral bisoxazoline group may be coupled to the inorganic substrate by a single tether group. The chiral bisoxazoline group may have structure Ia, Ib, Ic or Id.

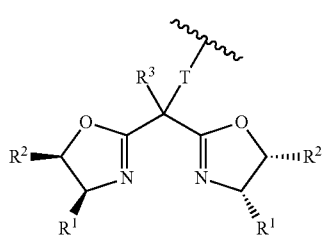

Ia

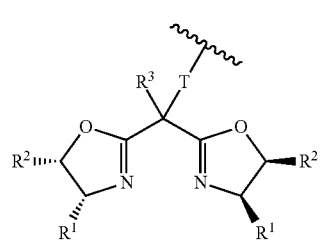

Ib

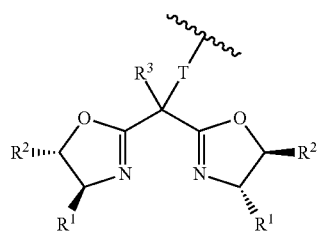

Ic

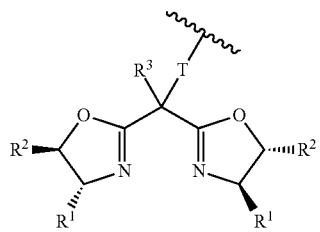

Id

In structure Ia to Id, $R^1$ may be a bulky group, and may be sufficiently bulky that a chiral catalyst comprising the heterogeneous chiral catalyst precursor complexed with a metal species capable of catalysing a chemical reaction is capable of catalysing the reaction to generate a chiral product. The chiral catalyst may be capable of catalysing the reaction to generate the chiral product with high enantiomeric excess. The chiral catalyst may have high reactivity for the reaction. $R^1$ may be an alkyl group, for example a C1 to C12 alkyl group, or an aryl group, an alkylaryl group or an arylalkyl group, for example a C6 to C12 aryl group or a C7 to C12 arylalkyl or alkylaryl group. $R^2$ may be hydrogen or it may be an alkyl group, for example a C1 to C12 alkyl group, or an aryl group, for example a C6 to C12 aryl group, or an arylalkyl or alkylaryl group, for example a C7 to C12 arylalkyl or alkylaryl group, or it may be some other group. $R^1$ and $R^2$ may be taken together with the carbon atoms to which they are attached to form a cyclic structure, for example a C5-C7 cyclic structure. They may for example form a benzocyclopentyl structure, such as structure Ie or If. $R^3$ may be an alkyl group, for example a C1 to C12 alkyl group, or an aryl group, for example a C6 to C12 aryl group, or an arylalkyl or alkylaryl group, for example a C7 to C12 arylalkyl or alkylaryl group. T is a tether group for coupling to the inorganic substrate. The carbon atoms to which $R^1$ and $R^2$ are attached may also, independently, have a hydrogen atom, or an alkyl group, for example methyl, ethyl, propyl, isopropyl or butyl group, attached thereto.

In one embodiment, $R^1$ is t-butyl and $R^2$ is methyl.

In another embodiment the chiral bisoxazoline group has a structure selected from the group consisting of Ie and If.

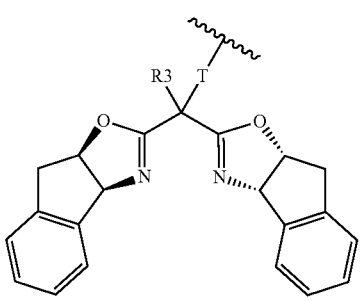

Ie

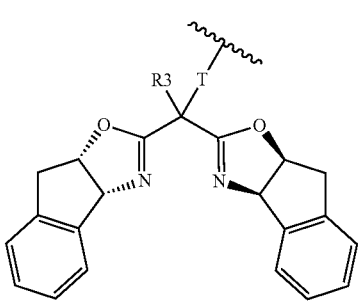

Tether group T may comprise a coupling group for coupling to the inorganic substrate and a linker group for linking the coupling group to the $CR^3$ group. The coupling group may be any suitable group for coupling to the inorganic substrate, and may for example comprise a silicon atom. It may be $SiR^4{}_2$, $Si(OR^5)R^4$, or $Si(OR^5)_2$, wherein $R^4$ and $R^5$ may independently be linear or branched alkyl groups, for example C1 to C12 alkyl groups, or aryl groups, for example C6 to C12 aryl groups. The linker group may an alkylene group [—$(CH_2)_n$—], example a C1 to C12 alkylene group, or an arylene group, for example a C6 to C12 arylene group such as [—$C_6H_4$—] or an alkylarylene or arylalkylene group, for example a C7 to C12 alkylarylene or arylalkylene group such as [—$CH_2C_6H_4$—$(CH_2)_n$—]. It may be for example —$C_3H_6$—. Alternatively it may be ether [—$(CH_2)_n$—O—$(CH_2)_m$—], carbamate [—$(CH_2)_n$—OC(O)NH—$(CH_2)_m$—] or amide [—$(CH_2)_n$—C(O)NH—$(CH_2)_m$—], or some other suitable group.

In another embodiment the tether group comprises —$C_3H_6Si$—. The silicon atom may have two other groups attached to it, which may be, independently, alkyl groups, aryl groups, alkoxy groups, aryloxy groups, OH groups or halo groups.

The inorganic substrate may be porous, and may be mesoporous. It may have pores that are between about 2 and 50 nm in diameter. The inorganic substrate may be particulate, and may have a particle size between about 100 nm and 200 microns. The inorganic substrate may comprise a ceramic, or a metal oxide or a mixed metal oxide. The metal may be for example titanium, silicon, germanium, aluminium or some other suitable metal. The inorganic substrate may be silica, and may be mesoporous silica. It may in particular be siliceous microcellular foam (MCF). In addition to the chiral bisoxazoline group, the inorganic substrate may comprise a hydrophobic group. The hydrophobic group may be any of the commonly known silane-based hydrophobic groups, derived from alkyl silanes of structure $SiR^4{}_n(OR^5)_{4-n}$ (an alkyl alkoxysilane) or $SiR^4{}_n(X)_{4-n}$ (an alkylhalosilane) or $R^4{}_nR^6{}_{3-n}SiOSiR^6{}_{3-n}R^4{}_n$ (disiloxane) or $R^4{}_nR^6{}_{3-n}SiNH SiR^6{}_{3-n}R^4{}_n$ (disilazane) where $R^4$, $R^5$ and $R^6$ are, independently, linear or branched alkyl groups, for example C1 to C12 alkyl groups, or aryl groups, for example C6 to C12 aryl groups, X is a halogen such as Cl, Br or I and n is 1, 2 or 3. The hydrophobic groups may be for example trimethylsilyl groups. Most free silanol groups (Si—OH) may be capped with hydrophobic groups. The number of free silanol groups (i.e. silanol groups not capped with hydrophobic groups) may be sufficiently low to reduce interactions between the chiral bisoxazoline group and free silanol groups. The distribution of bisoxazoline groups on the inorganic substrate may be uniform or homogeneous. The number of free silanol groups may be sufficiently low that the distribution of bisoxazoline groups on the inorganic substrate is uniform or homogeneous. The number of hydrophobic groups may be in the range of about 0.2 to 2 mmol/g. The number of hydrophobic groups may be such that a catalyst made from the heterogeneous chiral catalyst precursor is capable of catalysing a reaction with high enantiomeric excess, or with a desired level of enantiomeric excess In a second aspect of the invention there is provided a heterogeneous chiral catalyst comprising a heterogeneous chiral catalyst precursor according to the first aspect of the invention complexed with a metal species. The bisoxazoline group of the heterogeneous chiral catalyst precursor may be complexed with the metal species. The heterogeneous chiral catalyst may be capable of catalysing a chemical reaction, for example cyclopropanation, cnc-reaction, Diels-Alder reaction, allylic substitution, aziridination reactions, Mukaiyama aldol reaction and new asymmetric reactions such as enantioselective Henry reaction (*J. Am. Chem. Soc.* 2003, 12692) and enantioselective conjugate addition of carbamates for the synthesis of β-amino acids (*J. Am. Chem. Soc.* 2004 9188). The chemical reaction may be capable of generating a chiral product, and may be capable of generating a chiral product with high enantiomeric excess. It may be capable of generating the product with high reactivity.

The metal species may be any suitable catalytic metal species that is capable of being complexed to a bisoxazoline species. The metal species may be for example Cu(I), Cu(II), Mg(II) or Pd(II) or some other metal species.

In one embodiment the metal species is Cu(I).

In a third aspect of the invention there is provided a process for making a heterogeneous chiral catalyst precursor comprising coupling a chiral bisoxazoline to an inorganic substrate through a single group.

The chiral bisoxazoline may have structure IIa, IIb, IIe, IId, IIe or IIf, wherein $R^1$, $R^2$ and $R^3$ are as defined earlier, and T' is a group capable of coupling to the inorganic substrate.

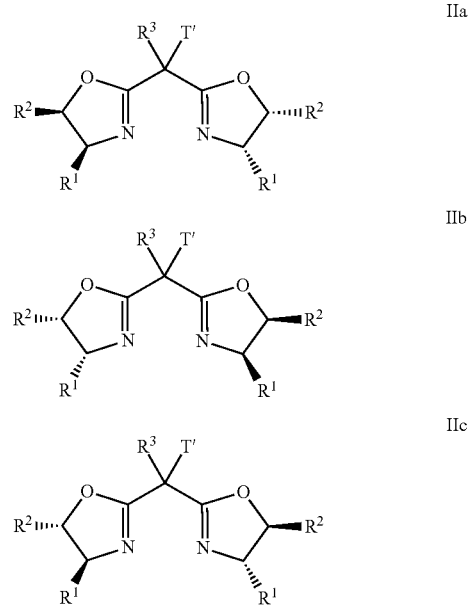

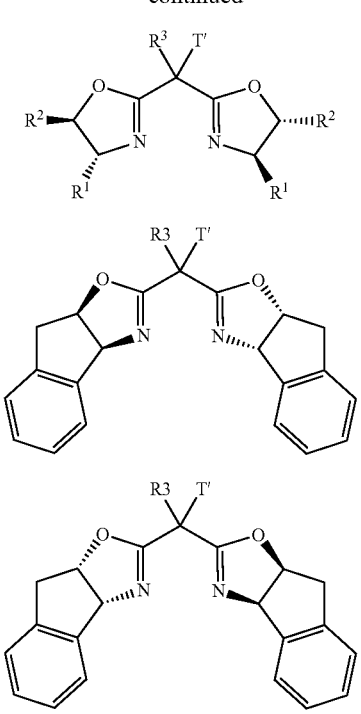

T' may comprise a coupling portion capable of coupling to the inorganic substrate and a linker group for linking the coupling group to the CR³ group. T' may form tether group T (as described earlier) on coupling with the inorganic substrate The coupling portion may be capable of producing the coupling group described in the first aspect on reacting with the inorganic substrate. It may be $Si(OR^4)(R^5)_2$, $Si(OR^4)_2R^5$, or $Si(OR^4)_3$, wherein $R^4$ and $R^5$ are, independently, linear or branched alkyl groups, for example C1 to C12 alkyl groups, or aryl groups, for example C6 to C12 aryl groups. The linker group may be as described earlier.

In an embodiment the tether group is —$C_3H_6Si(OR^4)_3$.

The process may additionally comprise reacting the inorganic substrate with a hydrophobing agent. The hydrophobing agent may be an alkyl silane of structure $SiR^4{}_n(OR^5)_{r-n}$ (an alkyl alkoxysilane) or $SiR^4{}_n(X)_{4-n}$ (an alkylhalosilane) or $R^5{}_nR^6{}_{3-n}SiOSiR^6{}_{3-n}R^5{}_n$ (disiloxane) or $R^4{}_nR^6{}_{3-n}SiNH SiR^6{}_{3-n}R^4{}_n$ (disilazane) where $R^4$, $R^5$ and $R^6$ are, independently, linear or branched alkyl groups, for example C1 to C12 alkyl groups, or aryl groups, for example C6 to C12 aryl groups, X is a halogen such as Cl and n is 1, 2 or 3. The step of reacting with the inorganic substrate may be performed before, during or after the step of coupling the chiral bisoxazoline to the inorganic substrate. Thus the hydrophobing agent may be reacted with the inorganic substrate in a separate step before or after the coupling step, or the hydrophobing agent may be mixed with the chiral bisoxazoline to form a coupling mixture, and the coupling mixture then exposed to the inorganic substrate. Alternatively, an inorganic substrate having hydrophobic groups may be used in the process.

The inorganic substrate may be as described for the first aspect of the invention. For example it may be mesoporous silica, such as MCF.

The present invention also provides a heterogeneous chiral catalyst precursor when made by the process of the third aspect of the invention.

In a fourth aspect of the invention there is provided a process for making a heterogeneous chiral catalyst comprising making a heterogeneous chiral catalyst precursor according to the process of the third aspect of the invention and treating the heterogeneous chiral catalyst precursor with a metal species. The metal species may be any suitable catalytic metal species that is capable of being complexed to a bisoxazoline species. The metal species may be for example Cu(I), Cu(II), Mg(II) or Pd(II), or some other metal species.

In one embodiment the metal species is Cu(I).

In a fifth aspect of the invention there is provided a process for making a heterogeneous chiral catalyst comprising:
complexing a chiral bisoxazoline with a metal species to form a complexed chiral bisoxazoline; and
coupling the complexed chiral bisoxazoline to an inorganic substrate.

The chiral bisoxazoline may have any one of structures IIa to IIf, and may be as described earlier. The metal species and the inorganic substrate may be as described earlier. The complexed chiral bisoxazoline may be capable of functioning as a catalyst.

In a sixth aspect of the invention there is provided a heterogeneous chiral catalyst when made by the process of the fourth or fifth aspect of the invention.

In a seventh aspect of the invention there is provided a method for catalysing reaction of a starting material to a product comprising exposing the starting material to a heterogeneous chiral catalyst according to the invention. The method may also comprise exposing the starting material to a reagent. Examples of reactions which may be catalysed according to this aspect include asymmetric cyclopropanation, ene-reaction, Diels-Alder reaction, allylic substitution, aziridination reactions, Mukaiyama aldol reaction or new asymmetric reactions such as enantioselective Henry reaction or enantioselective conjugate addition of carbamates for the synthesis of β-amino acids.

The invention also provides a product of a reaction that has been catalysed by a heterogeneous chiral catalyst according to the invention. An example of such a product is an asymmetric substituted cyclopropane when made by the method of the seventh aspect of the invention.

BRIEF DESCRIPTION OF THE FIGURES

Preferred embodiments of the present invention will now be described, by way of example only, with reference to the accompanying figures, wherein.

DETAILED DESCRIPTION OF THE PREFERRED EMBODIMENTS

Figure 1:
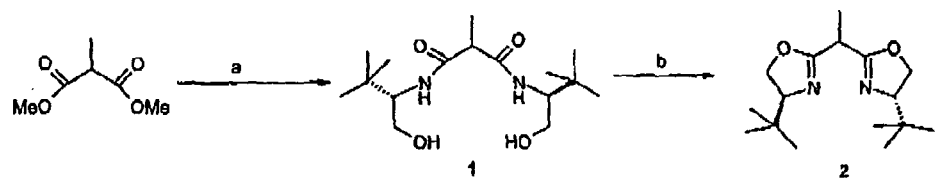
FIG. 1 shows a scheme for making a chiral bisoxazoline which may be used for making a heterogeneous chiral catalyst according to the present invention.

The present invention is based on the surprising and unexpected finding that chiral bisoxazolines synthesized with one methyl substituent at the carbon bridge, when covalently immobilised onto mesoporous silica supports, provides greatly improved enantioselectivity and reactivity.

A general formula for a typical heterogeneous chiral catalyst according to the invention is given by structure III: G-T-S, where G is one of structures Va to Vf shown below. It may be prepared either by reacting a metal species with a heterogeneous chiral catalyst precursor comprising a bisoxazoline of structure I coupled to an inorganic substrate, or by coupling a complexed chiral bisoxazoline of structure IV: G-T' to a suitable inorganic substrate, where G is one of structures Va to Vf shown below

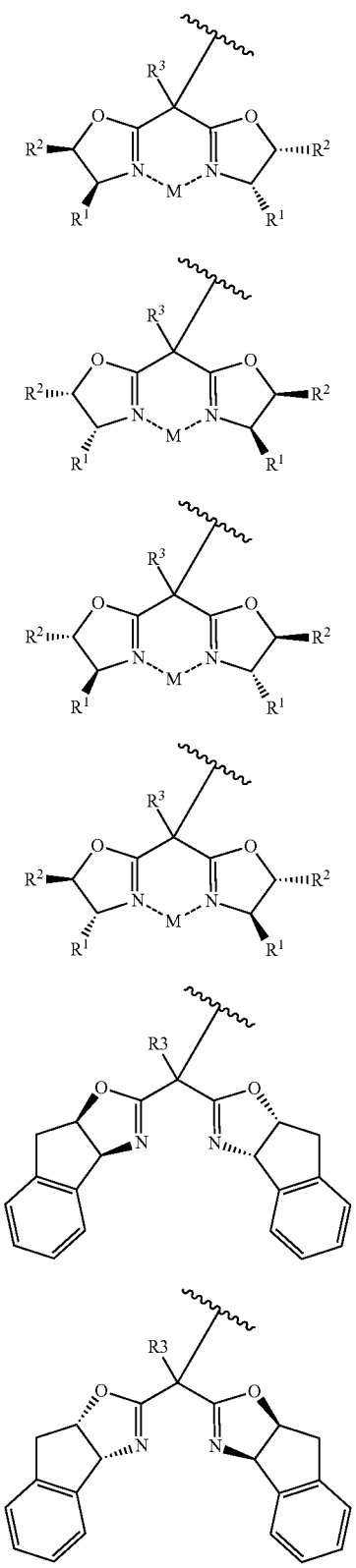

Compounds with structures I, III and IV may be (+) or (−) isomers.

In structures I to IV:

$R^1$ may be a bulky group, and may be sufficiently bulky that, when complexed with a metal species capable of catalysing a chemical reaction, the reaction is capable of generating a chiral product. The chiral product may have an enantiomeric excess of greater than about 10%, or greater than about 20, 30, 40, 50, 60, 70, 80, 90, 95, 96, 97, 98, 99, 99.5, 99.75 or 99.9%. $R^1$ may be an alkyl group, for example a C1 to C12 alkyl group, or an aryl group, an alkylaryl group or an arylalkyl group, for example a C6 to C12 aryl group or a C7 to C12 arylalkyl or alkylaryl group. The alkyl group may have between about 1 and 12 carbon atoms, or between about 1 and 6, 1 and 4, 3 and 12, 6 and 12 or 4 and 8 carbon atoms, and may have 1, 2, 3, 4, 5, 6, 7, 8, 9, 10, 11 or 12 carbon atoms, or more than 12 carbon atoms. The aryl group may have between 6 and 12 carbon atoms, or between 6 and 9, 9 and 12 or 8 and 10 carbon atoms, and may have 6, 7, 8, 9, 10, 11 or 12 carbon atoms, or more than 12 carbon atoms. The alkylaryl or arylalkyl group may have between 7 and 12 carbon atoms, or between 9 and 12, 7 and 9 or 9 and 12 carbon atoms, and may have 7, 8, 9, 10, 11 or 12 carbon atoms, or more than 12 carbon atoms. If $R^1$ is alkyl it may be straight chain or branched chain or may be alicyclic. It may for example be isopropyl, isobutyl, t-butyl, neopentyl, isopentyl, cyclohexyl, cyclopentyl, norbornyl, adamantyl or some other suitable group. If $R^1$ is aryl, it may be phenyl, biphenyl, naphthyl, and may be a substituted aryl, for example alkylphenyl (e.g. benzyl, t-butylphenyl). $R^1$ may also be a heterocyclic group, or a substituted heterocyclic group. The carbon atoms attached to the $R^1$ groups may be the same chirality, and may be both (S) or both (R).

$R^2$ may be hydrogen or it may be an alkyl group, for example a C1 to C12 alkyl group, or an aryl group, for example a C6 to C12 aryl group, or it may be some other group. $R^2$ may be a bulky group or a non-bulky group, and in addition to the examples described for $R^1$ may also be n-alkyl with a chain length of between 1 and 12 carbon atoms or more, for example methyl, ethyl, propyl, butyl, t-butyl, benzyl or phenyl.

$R^1$ and $R^2$ may be taken together with the carbon atoms to which they are attached to form a cyclic structure, for example a C5-C7 cyclic structure. They may for example form a benzocyclopentyl structure, such as in structure Ie or If. Other suitable cyclic structures may include, for example, cyclopentyl, cyclohexyl, cycloheptyl, benzocyclohexyl, naphthocyclopentyl or naphthocyclohexyl.

Each of the carbon atoms to which $R^1$ and $R^2$ are attached may also, independently, have a hydrogen atom, or an alkyl group, for example methyl, ethyl, propyl, isopropyl or butyl group, attached thereto, or may have some other suitable group attached thereto. Thus for example the carbon to which $R^1$ is attached may also have a methyl group attached thereto and the carbon to which $R^2$ is attached may also have a hydrogen atom attached thereto, or the carbon to which $R^1$ is attached may also have a hydrogen atom attached thereto and the carbon to which $R^2$ is attached may also have a methyl group attached thereto, or both the carbon atom to which $R^1$ is attached and the carbon atom to which $R^2$ is attached may have methyl groups attached thereto, or both the carbon atom to which $R^1$ is attached and the carbon atom to which $R^2$ is attached may have hydrogen atoms attached thereto.

$R^3$ may be an alkyl group, for example a C1 to C12 alkyl group, or an aryl group, for example a C6 to C12 aryl group, or it may be some other group. $R^2$ may be a bulky group or a non-bulky group, and in addition to the examples described for R$^1$ may also be n-alkyl with a chain length of between 1 and 12 carbon atoms or more, for example methyl, ethyl, propyl, or butyl.

T is a tether group for coupling to the inorganic substrate. T may comprise a coupling group for coupling to the inorganic substrate and a linker group for linking the coupling group to the CR$^3$ group. The coupling group may be any suitable group for coupling to the inorganic substrate, and may for example comprise a silicon atom. It may be SiR$^4{}_2$, Si(OR$^5$)R$^4$, or Si(OR$^5$)$_2$, wherein R$^4$ and R$^5$ may independently be as described for R$^2$ above. For example the coupling group may be Si(OMe)$_2$, SiMe(OMe), Si(OEt)$_2$, SiMe(OEt) or SiEt(OEt). The linker group may an alkylene group [—(CH$_2$)$_n$—] or an arylene group, and may comprise between 1 and 12 carbon atoms. If the linker group is an alkylene group it may be linear, branched or cyclic, and may have between 1 and 12, 1 and 10, 1 and 8, 1 and 6, 1 and 4, 2 and 12 or 6 and 12 carbon atoms, and may have 1, 2, 3, 4, 5, 6, 7, 8, 9, 10, 11 or 12 carbon atoms. It may be for example methylene, 1,2-ethanediyl, 1,3-propanediyl, 1,4-butanediyl, 1,5-pentanediyl, 1,6-hexanediyl, 1-methyl-1,5-pentanediyl, 2-methyl-1,5-pentanediyl, 1,4-cyclohexanediyl or some other alkylene or cycloalkylene group. If the linker is an aryl group it may be monocyclic or polycyclic, and may be for example phenylene, biphenylene or naphylene, e.g. [—CH$_2$C$_6$H$_4$—(CH$_2$)$_n$—]. Alternatively it may be ether [—(CH$_2$)$_n$—O—(CH$_2$)$_m$—], carbamate [—(CH$_2$)$_n$—OC(O)NH—(CH$_2$)$_m$—] or amide [—(CH$_2$)$_n$—C(O)NH—(CH$_2$)$_m$—], or some other suitable group. In the above formulae, n and m may independently be between about 1 and 12, and may be between 1 and 10, 1 and 8, 1 and 6, 1 and 4, 4 and 12, 6 and 12 or 4 and 8, and may independently be 1, 2, 3, 4, 5, 6, 7, 8, 9, 10, 11 or 12.

T' is a group capable of coupling to the inorganic substrate. T' may comprise a coupling portion capable coupling to the inorganic substrate and a linker group for linking the coupling group to the CR$^3$ group. T' may form tether group T (as described above) on coupling with the inorganic substrate. The coupling portion may be capable of producing the coupling group described in the first aspect on reacting with the inorganic substrate. It may be Si(OR$^5$)(R$^4$)$_2$, Si(OR$^5$)R$^4$, or Si(OR$^5$)$_3$, wherein R$^4$ and R$^5$ are as described above. For example it may be Si(OMe)$_3$, SiMe(OMe)$_2$, Si(OEt)$_3$, SiMe(OEt)$_2$ or SiEt(OEt)$_2$ The linker group may be as described above.

M may be a metal species and may be a catalytic metal species. It may be capable of complexing with the bisoxazoline group of structure I. It may be electrically neutral or it may be an ion, such as a positive ion. It may have a charge of 1, 2, 3 or 4. It may be for example Cu(I), Cu(II), Mg(II) or Pd(II) or some other metal species.

S is an inorganic substrate. The inorganic substrate may be porous, and may be mesoporous. It may have pores with diameter between about 2 and 50 nm. The pores may be between about 2 and 40, 2 and 30, 2 and 20, 2 and 10, 10 and 50, 20 and 50, 30 and 50, 5 and 50, 5 and 20 or 10 and 20 nm, and may be about 2, 3, 4, 5, 6, 7, 8, 9, 10, 15, 20, 25, 30, 35, 40, 45 or 50 nm in diameter. The inorganic substrate may be particulate, for example microparticulate or nanoparticulate, and may have a particle size between about 100 nm and 200 microns. The particle size may be between about 500 nm and 200 microns, or between about 1 and 200, 10 and 200, 50 and 200, 100 and 200, 1 and 100, 1 and 50 or 1 and 10 microns or between about 100 nm and 100 microns, 100 nm and 10 microns, 100 nm and 1 micron or 500 nm and 1 micron, and may be about 100, 200, 300, 400, 500, 600, 700, 800 or 900 microns, or about 1, 2, 3, 4, 5, 6, 7, 8, 9, 10, 20, 30, 40, 50, 60, 70, 80, 90, 100, 110, 120, 130, 140, 150, 160, 170, 180, 190 or 200 microns. The particle size distribution may be narrow, or it may be broad. The inorganic substrate may comprise a ceramic, or a metal oxide or a mixed metal oxide. The metal may be for example titanium, silicon, germanium, aluminium or some similar metal. The inorganic substrate may be silica, and may be mesoporous silica. It may in particular be siliceous microcellular foam (MCF). MCF is a suitable substrate since it has large surface area, interconnected large pores and easy control of the pore size. The inorganic substrate may comprise a silica foam according to the copending application entitled "Mesocellular Foam Particles". The inorganic substrate should be capable of coupling with the coupling portion. Alternatively the inorganic substrate may be a metal, for example a noble metal eg gold, platinum or palladium. In this case the coupling portion may be capable of coupling with a noble metal. It may for example be a thiol or a disulfide. The metal may be finely porous, microporous, particulate or nanoporous. It may have pores between about 1 and 100 nm or between 1 and 50, 1 and 20, 1 and 10, 1 and 5, 5 and 100, 20 and 100, 50 and 100, 5 and 50 or 10 and 50 nm, and may have pores about 1, 2, 3, 4, 5, 10, 15, 20, 25, 30, 40, 50, 60, 70, 80, 90 or 100 nm.

Substrate S may be hydrophobic. It may be hydrophobed by reacting the inorganic substrate with a hydrophobing agent. The hydrophobing agent may be an alkyl silane of structure SiR$^4{}_n$(OR$^5$)$_{4-n}$ (an alkyl alkoxysilane) or SiR$^4{}_n$(X)$_{4-n}$ (an alkylhalosilane), as described earlier, or it may be a disiloxane or disilazane, for example hexamethyldisiloxane or hexamethyldisilazane. The step of hydrophobing may generate hydrophobic groups on the substrate. The hydrophobic groups may be trialkylsilyl groups, or dialkylalkoxy groups or some other hydrophobic groups, and may be for example trimethylsilyl groups. The step of reacting with the inorganic substrate may be performed before, during or after the step of coupling the chiral bisoxazoline to the inorganic substrate. Thus the hydrophobing agent may be reacted with the inorganic substrate in a separate step before the coupling step, or the hydrophobing agent may be mixed with the chiral bisoxazoline to form a coupling mixture, and the coupling mixture then exposed to the substrate. There may be between about 0.2 and 2 mmol hydrophobic groups per gram of inorganic substrate, or between about 0.2 and 1.5, 0.2 and 1, 0.2 and 0.5, 0.5 and 2, 1 and 2 or 0.5 and 1.5 mmol/g hydrophobic groups, and may be about 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2 mmol hydrophobic groups per gram of inorganic substrate, or may be more than 2 mmol hydrophobic groups per gram of inorganic substrate.

The inventors have found that when an inorganic substrate is used that has not been hydrophobed, the resulting catalyst produced lower enantiomeric excess than when an at least partially hydrophobed inorganic substrate is used. Thus the level of hydrophobic groups should be sufficient to generate a catalyst capable of catalysing a reaction with high enantiomeric excess, or with a desired level of enantiomeric excess.

In the present invention, there may be a high loading of bisoxazoline groups on the inorganic substrate. There may be between about 0.01 and 1 mmol/g, or between about 0.05 and 1, 0.1 and 1, 0.2 and 1, 0.5 and 1, 0.01 and 0.5, 0.01 and 1, 0.1 and 0.5 or 0.2 and 0.5 mmol/g, and may be about 0.01, 0.05, 0.1, 0.15, 0.2, 0.25, 0.3, 0.35, 0.4, 0.45, 0.5, 0.6, 0.7, 0.8, 0.9 or 1 mmol/g.

The heterogeneous chiral catalyst of the present invention may be used to catalyse chemical reactions and may catalyse production of chiral products. A starting material for a chemical reaction may be exposed to the catalyst. The starting material may be in solution in a solvent. The reaction may be conducted at low temperature, ambient temperature or elevated temperature, and may be at between about 0 and 100° C., or between about 0 and 50, 0 and 20, 0 and 10, 10 and 100, 25 and 100, 50 and 100, 10 and 50 or 20 and 50° C., and may be at about 0, 5, 10, 15, 20, 25, 30, 35, 40, 45, 50, 55, 60, 65, 70, 75, 80, 85, 90, 95 or 100° C. or may be greater than about 100° C. or less than about 0° C. The catalyst may be combined with the starting material or the solution, and may be mixed, stirred, shaken or otherwise agitated with the starting material or the solution. Alternatively the starting material or solution may be passed through the catalyst, whereby the catalyst is constrained in a housing, for example an HPLC column housing, a column housing or some other housing. In this case the reaction may be conducted at high pressure, and the starting material may be passed through the catalyst at high pressure. The high pressure may be between about 1 and 200 atmospheres, or between about 1 and 100, 1 and 50, 1 and 20, 1 and 10, 10 and 200, 50 and 200, 100 and 200, 150 and 200, 10 and 100 or 50 and 100 atmospheres, and may be about 1, 2, 3, 4, 5, 10, 15, 20, 25, 30, 35, 40, 45, 50, 60, 70, 80, 90.100, 110, 120, 130, 140, 150, 160, 170, 180, 190 or 200 atmospheres, or may be at some other pressure. Different optical isomers of the heterogeneous chiral catalyst may catalyse production of chiral products with opposite chirality. The heterogeneous chiral catalyst may be separated from a reaction mixture, for example by one or more of filtration, settling, decanting or centrifuging. It may then be washed and or dried. It may be reused in subsequent reactions, and may be reused multiple times, for example 1, 2, 3, 4, 5, 6, 7, 8, 9 or 10 or more than 10 times.

EXAMPLE

The present invention will now be described with reference to a specific example, which should not be construed as in any way limiting the scope of the invention.

In this example, a chiral bisoxazoline with one methyl substituent at the carbon bridge was immobilized onto a mesoporous silica support. Surprisingly, the resulting BOX—Cu(I) catalyst showed very high enantioselectivity and reactivity for the asymmetric cyclopropanation of styrene.

Chiral bisoxazolines were immobilized onto mesoporous solids by one linker group. In order to achieve this, bisoxazoline 2 was synthesized with one methyl substituent at the carbon bridge (FIG. 1).

Figure 2:
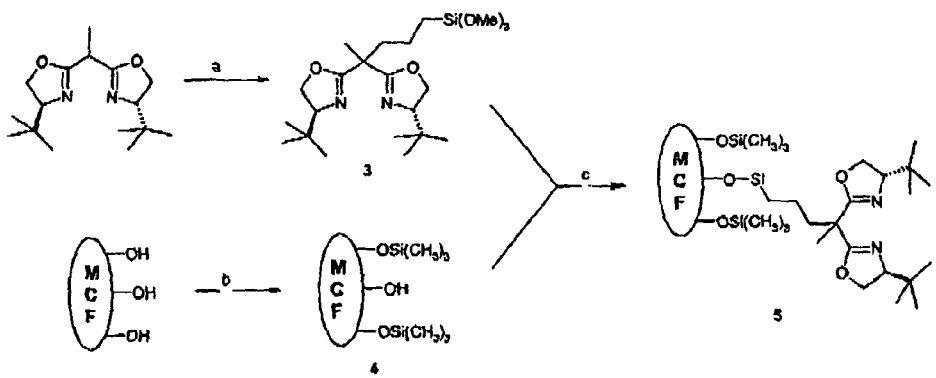
FIG. 2 shows a scheme for making a heterogeneous chiral catalyst according to the present invention.

This bisoxazoline ligand was then modified to obtain a trimethoxysilane group (FIG. 2). Bisoxazoline 2 was reacted with MeLi to give a lithiated product, which was reacted with 3-iodopropyltrimethoxysilane to give silane-modified bisoxazoline. The modified bisoxazoline 3 was easily anchored onto siliceous mesocellular foam (MCF) with a high loading (0.26 mmol/g) (FIG. 2).

The surface of MCF was partially modified with TMS (trimethylsilyl) groups before immobilization of bisoxazolines. HMDS (hexamethyldisiloxane) (0.4 mmol) was added to MCF (1.0 g) in toluene to produce TMS-modified MCF (0.8 mmol/g). This modification not only allowed for the uniform immobilization of bisoxazolines on the MCF surface, but also provided for ease of control in the amount of ligand loaded.

The heterogenized bisoxazoline formed a bisoxazoline-copper (I) complex by reaction with copper (I) triflate. The resulting heterogenized catalyst was examined for the asymmetric cyclopropanation of styrene (see Table I). The MCF-supported bisoxazoline-copper (I) complex 5:CuOTf provided excellent enantioselectivity and reactivity. The catalyst offered 95% ee for trans isomer and 91% ee for cis isomer. The heterogenized catalyst was recycled four times without loss of enantioselectivity and reactivity. Even with a very small amount of heterogenized catalysts (0.2 mol %), high enantioselectivity (95% ee for trans isomer) and reactivity were attained. The inventors believe that this system is the best silica-supported bisoxazoline catalyst yet developed.

TABLE 1

Asymmetric cyclopropanation of styrene by 5:CuOTf.[a]

| Catalyst | Run # | Catalyst (mol %) | Styrene/EDA | % Conversion[b] | Trans/Cis[b] | % ee Trans[c] | % ee Cis[c] |
|---|---|---|---|---|---|---|---|
| 5:CuOTf | 1 | 2 | 1.2 | 100 | 65/35 | 95 | 92 |
|  | 2 | 2 | 1.2 | 100 | 65/35 | 95 | 91 |
|  | 3 | 2 | 1.2 | 100 | 65/35 | 95 | 91 |
|  | 4 | 2 | 1.2 | 100 | 64/36 | 94 | 90 |
|  | 5 | 2 | 1.2 | 100 | 64/36 | 95 | 89 |
| 5:CuOTf | 1 | 0.2 | 1.2 | 100 | 66/35 | 94 | 91 |

[a]All reactions were carried out under argon.
[b]Determined by GC.
[c]Determined by GC with a Chiraldex-B column.

In conclusion, chiral oxazoline ligands were effectively immobilized onto mesoporous silica supports. The heterogenized catalyst showed high enantioselectivity and reactivity for asymmetric cyclopropanation of styrene. It was also successfully recycled four times, without losing any enantioselectivity and reactivity. This immobilization method can be widely applied to other types of chiral bisoxazolines. The immobilized chiral bisoxazoline catalysts are expected to show high enantioselectivity for various asymmetric reactions.

EXPERIMENTAL DETAILS

Synthesis of Bisoxazoline with One Methyl Group at the Carbon Bridge (Bisoxazoline 2)

Dimethyl methylmalonate (1.78 g, 12.2 mmol) and (S)-tert-leucinol (3.0 g, 25.6 mmol) were heated to 90° C. under an argon flow, which removed the methanol generated during the reaction. After 12 hr, white solids were obtained. To remove the remaining reactants, high vacuum was applied at 60° C. Dihydroxymethylmalonodiamide 1 (3.27 g, 10.37 mmol) was obtained with a high yield (85%). A 100-ml Schlenk flask was charged with dihydroxymethylmalonodiamide 1 (2.87 g, 9.08 mmol), 4-(dimethylamino)pyridine (0.12 g, 0.99 mmol), and 40 ml of $CH_2Cl_2$. Triethylamine (6 ml, 43.5 mmol) was then added. A solution of p-toluenesulfonic chloride (3.77 g, 19.8 mmol) in 10 ml of $CH_2Cl_2$ was added. The resulting bright yellow solution was stirred at room temperature for 27 hr. It was diluted with 20 ml of $CH_2Cl_2$, and washed with saturated $NH_4Cl$. The aqueous layer was back-extracted with $CH_2Cl_2$ (3×30 ml). The combined organic extracts were washed with saturated $NaHCO_3$. The aqueous layer was back-extracted with $CH_2Cl_2$ (3×30 ml). The combined organic extracts were dried over $Na_2SO_4$, filtered and concentrated in vacuum. The concentrated liquors were purified by flash chromatography to give the product referred to here as bisoxazoline 2 (2.03 g, 7.26 mmol, 80% yield). $^1$H NMR (300 MHz, $CDCl_3$): δ=4.17 (m, 2H), 4.08 (m, 2H), 3.85 (m, 2H), 3.54 (q, J= 7.3 Hz, 1H), 1.48 (d, J=7.3 Hz, 3H), 0.881 (s, 9H), 0.878 (s, 9H). $^{13}$C NMR (300 MHz, $CDCl_3$): δ=165.5, 165.3, 75.5, 68.9, 34.0, 33.8, 25.7, 25.6, 15.2. Elemental analysis of $C_{16}H_{28}N_2O_2$: calculated=C, 68.53; H, 10.07; N, 9.99. found=C, 68.14; H, 10.22; N, 9.84.

Immobilization of Bisoxazoline 2 onto Mesoporous Silica

MeLi (0.516 ml, 1.6 M in $Et_2O$, 0.825 mmol) was added into a solution of bisoxazoline 2 (0.21 g, 0.75 mmol) in 10 ml of THF at −50° C. After stirring for 30 min, 3-iodopropyltrimethoxysilane (0.148 ml, 0.75 mmol) was added, and the solution was warmed to room temperature. After stirring for 2 days at room temperature, THF was evaporated and toluene was added. The toluene solution was added to MCF, which was partially modified by TMS using HMDS (0.4 mmol/g). The toluene suspension was then heated to 90° C. with stirring for 1 day, and filtered. IR (cm$^{-1}$): 2957, 1663, 1089, 842, 811, 460. Elemental analysis: found=C, 11.45; H, 2.25; N, 0.73. Loading of bisoxazoline: 0.26 mmol/g.

Farther Protection of MCF-Supported Bisoxazoline with HMDS

MCF-supported bisoxazoline was degassed at 80° C. overnight HMDS was then added to the solid under vacuum. The flask was then cooled down using liquid $N_2$ under vacuum. It was then sealed and warmed to room temperature. The flask was then placed in an oven at 75° C. for 5 hr. After the reaction, excess HMDS was removed under vacuum.

Cyclopropanation of Styrene by MCF-Supported Bisoxazoline (CuOTf)$_2$.toluene (0.011 mmol) or Cu(OTf)$_2$ (0.022 mmol) was added to the MCF-immobilized bisoxazoline (0.022 mmol) in $CH_2Cl_2$ (2 ml). The mixture was stirred at room temperature for 5 days. In the case of Cu(OTf)$_2$, diazoacetate (0.015 mmol) was added to reduce copper. After the addition of styrene (153 μl, 1.32 mmol), a solution of ethyl diazoacetate (1.1 mmol, diluted with 2 ml $CH_2Cl_2$) was added over 2 hr using a syringe pump. The mixture was then stirred for 1 hr and centrifuged. The solution portion was collected, and the trans/cis ratio and yield were determined by gas chromatography (GC). The enantiomeric excess was determined by GC using a Cyclodex-B column. The precipitate was then washed with $CH_2Cl_2$ (5 ml) and centrifuged three times. The recovered catalyst was used as the starting material for further experiments.

The invention claimed is:

1. A heterogenous chiral catalyst precursor comprising a chiral bisoxazoline group coupled to an inorganic substrate, said precursor being made by a process comprising coupling a chiral bisoxazoline to a hydrophobic inorganic substrate.

2. The precursor of claim 1 wherein the chiral bisoxazoline group is coupled to the inorganic substrate by a single tether group.

3. The precursor of claim 1 wherein the bisoxazoline is covalently bonded to the inorganic substrate.

4. The precursor of claim 1 wherein the chiral bisoxazoline group has a structure selected from the group consisting of Ia, Ib, Ic, Id, Ie and If

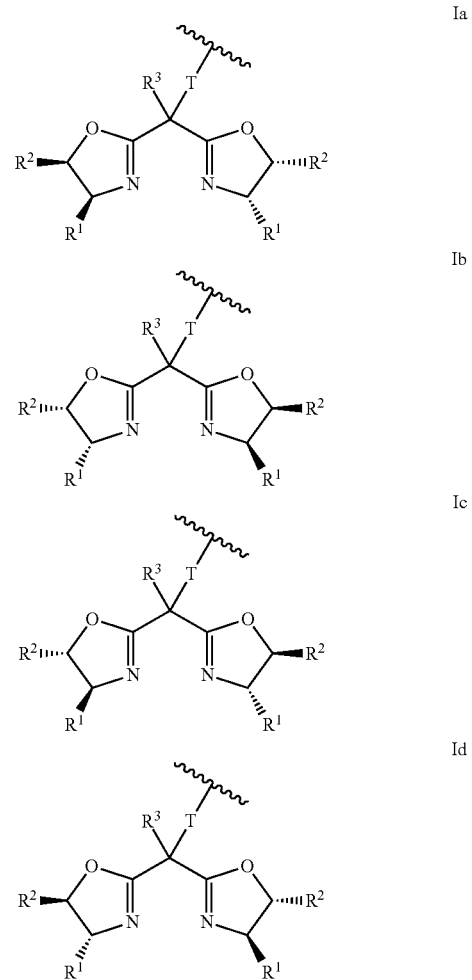

Ie

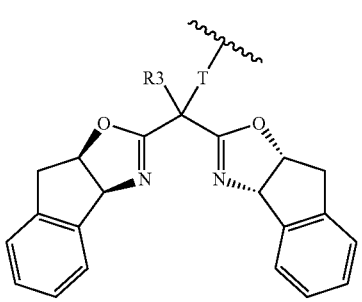

If

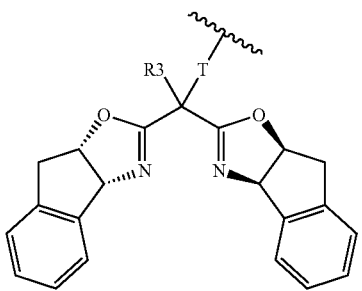

wherein
- $R^1$ is a bulky group and $R^2$ is selected from the group consisting of hydrogen, an alkyl group, an aryl group, an arylalkyl group and an alkylaryl group, or $R^1$ and $R^2$, taken together with the carbon atoms to which they are attached, form a cyclic structure,
- $R^3$ is selected from the group consisting of an alkyl group, an aryl group, an arylalkyl group and an alkylaryl group, and
- T is a tether group for coupling to the inorganic substrate.

5. The precursor of claim 4 wherein $R^1$ is selected from the group consisting of an alkyl group, an aryl group, an arylalkyl group and an alkylaryl group.

6. The precursor of claim 4 wherein $R^1$ is t-butyl, $R^2$ is hydrogen and $R^3$ is methyl.

7. The precursor of claim 1 wherein the chiral bisoxazoline group has a structure selected from the group consisting of Ia', Ib', Ic', Id', Ie' and If'

Ia'

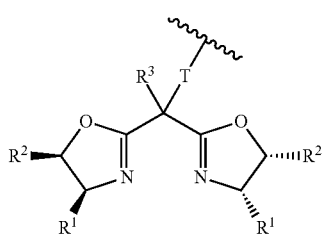

Ib'

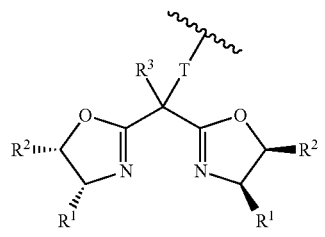

Ic'

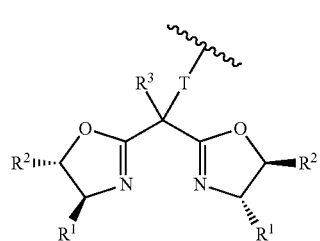

Id'

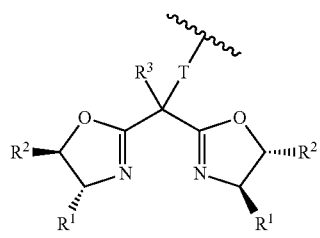

Ie'

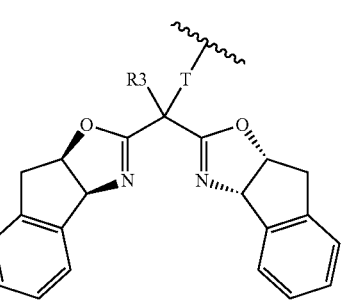

If'

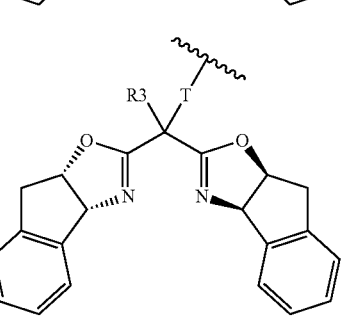

wherein
- $R^1$ is a bulky group and $R^2$ is selected from the group consisting of hydrogen, an alkyl group, an aryl group, an arylalkyl group and an alkylaryl group, or $R^1$ and $R^2$, taken together with the carbon atoms to which they are attached, form a cyclic structure,
- $R^3$ is selected from the group consisting of an alkyl group, an aryl group, an arylalkyl group and an alkylaryl group,
- T is a tether group for coupling to the inorganic substrate, and
- each of the carbon atoms to which $R^1$ and $R^2$ are attached also, independently, has a hydrogen atom or an alkyl group attached thereto.

8. The precursor of claim 4 or claim 7 wherein the tether group comprises a coupling group for coupling to the inorganic substrate and a linker group for linking the coupling group to the $CR^3$ group.

9. The precursor of claim 8 wherein the coupling group comprises a silicon atom.

10. The precursor of claim 8 wherein the linker group is selected from the group consisting of an alkylene group, an arylene, an alkylarylene group and an arylalkylene group.

11. The precursor of claim 8 wherein the linker group is —$C_3H_6$—.

12. The precursor of claim 1 wherein the inorganic substrate is porous.

13. The precursor of claim 1 wherein the inorganic substrate is mesoporous.

14. The precursor of claim 1 wherein the inorganic substrate comprises silica.

15. The precursor of claim 1 wherein the inorganic substrate comprises hydrophobic groups.

16. The precursor of claim 15 wherein the hydrophobic groups are trimethylsilyl groups.

17. The precursor of claim 15 wherein the number of hydrophobic groups is between 0.2 and 2 mmol per gram of inorganic substrate.

18. A heterogeneous chiral catalyst comprising a heterogeneous chiral catalyst precursor complexed with a metal species, said heterogeneous chiral catalyst precursor comprising a chiral bisoxazoline group coupled to an inorganic substrate, and said precursor being made by a process comprising coupling a chiral bisoxazoline to a hydrophobic inorganic substrate.

19. The catalyst of claim 18 wherein the chiral bisoxazoline group is coupled to the inorganic substrate by a single tether group.

20. The catalyst of claim 18 wherein the chiral bisoxazoline group has structure selected from the group consisting of Ia, Ib, Ic, Id, Ie and If as shown in claim 4 wherein:
$R^1$ is a bulky group and $R^2$ is selected from the group consisting of hydrogen, an alkyl group, an aryl group, an arylalkyl group and an alkylaryl group, or $R^1$ and $R^2$, taken together with the carbon atoms to which they are attached, form a cyclic structure,
$R^3$ is selected from the group consisting of an alkyl group, an aryl group, an arylalkyl group and an alkylaryl group, and
T is a tether group for coupling to the inorganic substrate.

21. The catalyst of claim 18 wherein the metal species is Cu(I).

22. The catalyst of claim 18 wherein the inorganic substrate comprises mesoporous silica.

23. A process for making a heterogeneous chiral catalyst precursor comprising coupling a chiral bisoxazoline to a hydrophobic inorganic substrate.

24. The process of claim 23 wherein said coupling is through a single tether group.

25. The process of claim 23 wherein the chiral bisoxazoline has a structure selected from the group consisting of IIa, IIb, IIc, IId, IIe and IIf

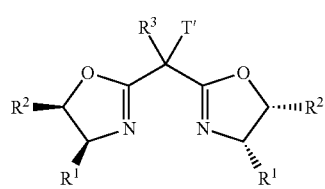

IIa

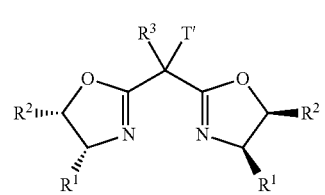

IIb

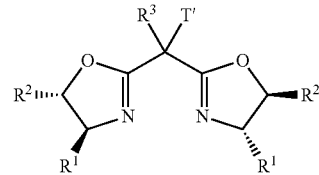

IIc

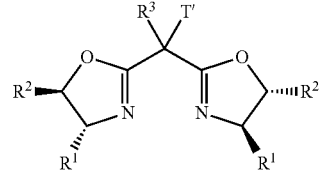

IId

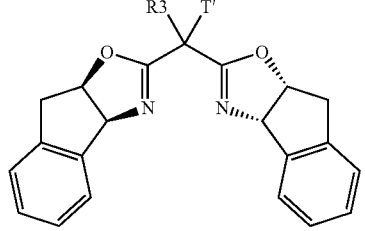

IIe

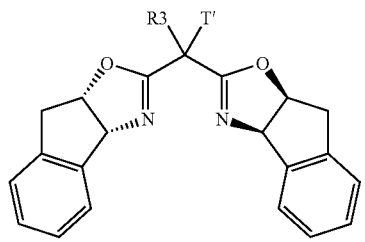

IIf wherein $R^1$ is a bulky group and $R^2$ is selected from the group consisting of hydrogen, an alkyl group, an aryl group, an arylalkyl group and an alkylaryl group, or $R^1$ and $R^2$, taken together with the carbon atoms to which they are attached, form a cyclic structure,
$R^3$ is selected from the group consisting of an alkyl group, an aryl group, an arylalkyl group and an alkylaryl group, and
T' is a group capable of coupling to the inorganic substrate.

26. The process of claim 25 wherein $R^1$ is selected from the group consisting of an alkyl group, an aryl group, an arylalkyl group and an alkylaryl group.

27. The process of claim 25 wherein $R^1$ is t-butyl, $R^2$ is hydrogen, $R^3$ is methyl and T' is trimethoxysilylpropyl.

28. The process claim 23 additionally comprising reacting an inorganic substrate with a hydrophobing agent to produce the hydrophobic inorganic substrate.

29. The process of claim 28 wherein the hydrophobing agent is selected from the group consisting of a silane and a siloxane.

30. The process of claim 23 wherein the hydrophobic inorganic substrate is hydrophobic mesoporous silica.

31. A process for making a heterogeneous chiral catalyst comprising coupling a chiral bisoxazoline to a hydrophobic inorganic substrate to make a heterogeneous chiral catalyst precursor and treating the heterogeneous chiral catalyst precursor with a metal species.

32. The process of claim 31 wherein said coupling is through a single tether group.

33. The process of claim 31 wherein the chiral bisoxazoline has a structure selected from the group consisting of IIa, IIb, IIc, IId, IIe and IIf as shown in claim 25 wherein:

R¹ is a bulky group and R² is selected from the group consisting of hydrogen, an alkyl group, an aryl group, an arylalkyl group and an alkylaryl group, or R¹ and R², taken together with the carbon atoms to which they are attached, form a cyclic structure, R³ is selected from the group consisting of an alkyl group, an aryl group, an arylalkyl group and an alkylaryl group, and T' is a group capable of coupling to the inorganic substrate.

34. The process of claim 31 wherein the metal species is Cu(I).

35. A heterogeneous chiral catalyst when made by a process comprising coupling a chiral bisoxazoline to a hydrophobic inorganic substrate to make a heterogeneous chiral catalyst precursor and treating the heterogeneous chiral catalyst precursor with a metal species.

36. The heterogeneous chiral catalyst of claim 35 wherein the chiral bisoxazoline has a structure selected from the group consisting of IIa, IIb, IIc, IId, IIe and IIf as shown in claim 25 wherein:

R¹ is a bulky group and R² is selected from the group consisting of hydrogen, an alkyl group, an aryl group, an arylalkyl group and an alkylaryl group, or R¹ and R², taken together with the carbon atoms to which they are attached, form a cyclic structure, R³ is selected from the group consisting of an alkyl group, an aryl group, an arylalkyl group and an alkylaryl group, and T' is a group capable of coupling to the inorganic substrate.

37. A method for catalysing reaction of a starting material to a product comprising exposing the starting material to a heterogeneous chiral catalyst comprising a heterogeneous chiral catalyst precursor complexed with a metal species, said heterogeneous chiral catalyst precursor comprising a chiral bisoxazoline group coupled to an inorganic substrate, said precursor being made by a process comprising coupling a chiral bisoxazoline to a hydrophobic inorganic substrate.

38. The method of claim 37 wherein the wherein the chiral bisoxazoline group has structure selected from the group consisting of Ia, Ib, Ic, Id, Ie and If as shown in claim 4 wherein:

R¹ is a bulky group and R² is selected from the group consisting of hydrogen, an alkyl group, an aryl group, an arylalkyl group and an alkylaryl group, or R¹ and R², taken together with the carbon atoms to which they are attached, form a cyclic structure, R³ is selected from the group consisting of an alkyl group, an aryl group, an arylalkyl group and an alkylaryl group, and T' is a group capable of coupling to the inorganic substrate.

39. The method of claim 37 wherein the reaction is an asymmetric cyclopropanation.

40. A chiral product when made by a reaction catalysed by a heterogeneous chiral catalyst comprising a heterogeneous chiral catalyst precursor complexed with a metal species, said heterogeneous chiral catalyst precursor comprising a chiral bisoxazoline group coupled to an inorganic substrate, and said precursor being made by a process comprising coupling a chiral bisoxazoline to a hydrophobic inorganic substrate.

41. The chiral product of claim 40 having enantiomeric excess greater than about 90%.

42. A heterogenous chiral catalyst precursor comprising a chiral bisoxazoline group coupled to an inorganic substrate, whereby said precursor is capable of complexing with Cu(I) to form a heterogeneous chiral catalyst, said catalyst being capable of catalysing a cyclopropanation reaction of an olefin with an azo compound with greater than 50% yield.

43. A heterogenous chiral catalyst precursor comprising a chiral bisoxazoline group coupled to an inorganic substrate, whereby said precursor is capable of complexing with Cu(I) to form a heterogeneous chiral catalyst, said catalyst being capable of catalysing a cyclopropanation reaction of an olefin with an azo compound with greater than 60% enantioselectivity.

44. A heterogeneous chiral catalyst comprising a heterogeneous chiral catalyst precursor complexed with a metal species, said heterogeneous chiral catalyst precursor comprising a chiral bisoxazoline group coupled to an inorganic substrate and said catalyst being capable of catalysing a cyclopropanation reaction of an olefin with an azo compound with greater than 50% yield.

45. A heterogeneous chiral catalyst comprising a heterogeneous chiral catalyst precursor complexed with a metal species, said heterogeneous chiral catalyst precursor comprising a chiral bisoxazoline group coupled to an inorganic substrate and said catalyst being capable of catalysing a cyclopropanation reaction of an olefin with an azo compound with greater than 60% enantioselectivity.

* * * * *

UNITED STATES PATENT AND TRADEMARK OFFICE
CERTIFICATE OF CORRECTION

PATENT NO. : 7,919,422 B2  Page 1 of 3
APPLICATION NO. : 11/885984
DATED : April 5, 2011
INVENTOR(S) : Jackie Y. Ying et al.

It is certified that error appears in the above-identified patent and that said Letters Patent is hereby corrected as shown below:

Column 2, lines 55-65, structure Ie should be

Ie

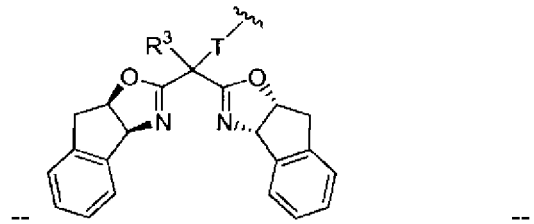

--

Column 3, lines 1-13, structure If should be

If

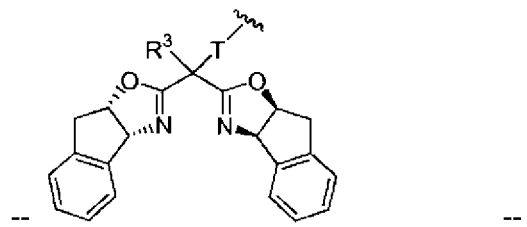

--

Column 3, line 23, "may an" should be -- may be an --

Column 3, line 24, "example" should be -- for example --

Column 3, lines 26 and 27, "arlylalkylene group" should be -- arylalkylene group -- both occurrences Column 4, line 19, "IIenry" should be -- Henry --

Column 4, line 37, "IIb, IIe, IId" should be -- IIb, IIc, IId --

Signed and Sealed this
Fifth Day of July, 2011

David J. Kappos
*Director of the United States Patent and Trademark Office*

Column 5, lines 10-28, structures IIe and IIf should be

IIe

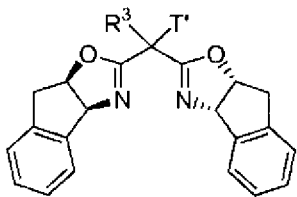

IIf

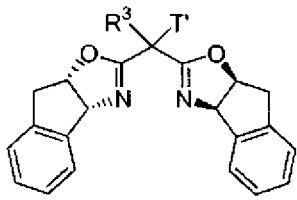

Column 5, line 33, "inorganic substrate" should be -- inorganic substrate. --

Column 7, lines 43-64, structures Ve and Vf should be

Ve

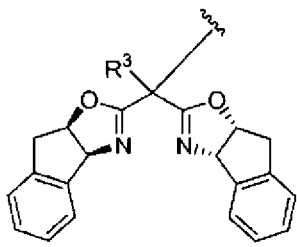

Vf

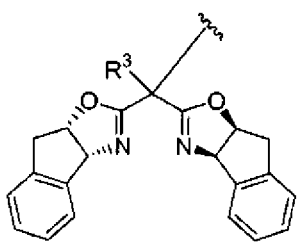

Column 9, line 13, "may an" should be -- may be an --

Column 9, line 35, "capable coupling" should be -- capable of coupling --

Column 9, line 44, "SiEt(()Et)₂" should be -- SiEt(()Et)$_2$. --

Claim 4, Column 15, lines 1-24, structures Ie and If should be

Ie
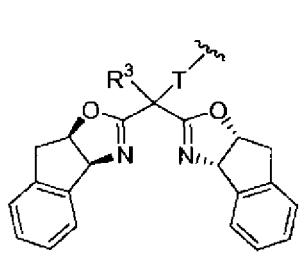
If
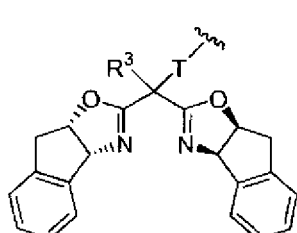
Claim 7, Column 16, lines 21-43, structures Ie and If should be
Ie
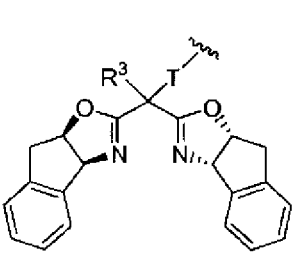
If
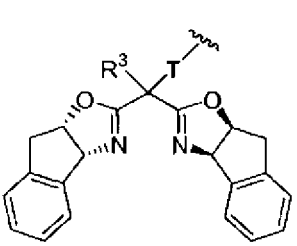
Claim 25, Column 18, lines 17-36, structures IIe and IIf should be
IIe
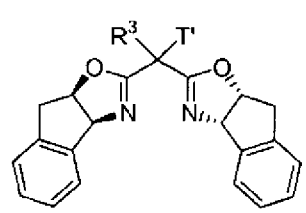
IIf
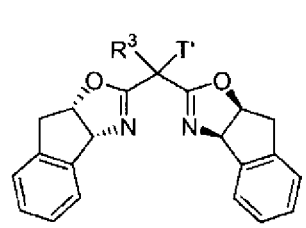
Claim 27, Column 19, line 51, "The process claim" should be -- The process of claim --
Claim 38, Column 19, line 38, "wherein the wherein the chiral" should be -- wherein the chiral --

UNITED STATES PATENT AND TRADEMARK OFFICE
CERTIFICATE OF CORRECTION

PATENT NO.        : 7,919,422 B2
APPLICATION NO.   : 11/885984
DATED             : April 5, 2011
INVENTOR(S)       : Jackie Y. Ying et al.

It is certified that error appears in the above-identified patent and that said Letters Patent is hereby corrected as shown below:

Column 2, lines 55-65, structure Ie should be

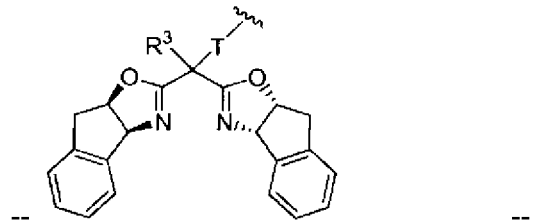

Column 3, lines 1-13, structure If should be

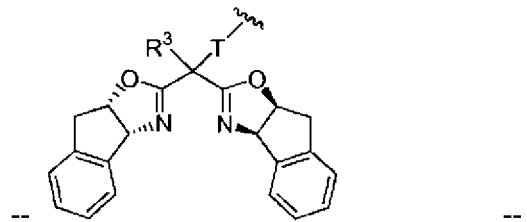

Column 3, line 23, "may an" should be -- may be an --

Column 3, line 24, "example" should be -- for example --

Column 3, lines 26 and 27, "arlylalkylene group" should be -- arylalkylene group -- both occurrences Column 4, line 19, "Ilenry" should be -- Henry --

Column 4, line 37, "IIb, IIe, IId" should be -- IIb, IIc, IId --

This certificate supersedes the Certificate of Correction issued July 5, 2011.

Signed and Sealed this
Twenty-third Day of August, 2011

David J. Kappos
*Director of the United States Patent and Trademark Office*

Column 5, lines 10-28, structures IIe and IIf should be
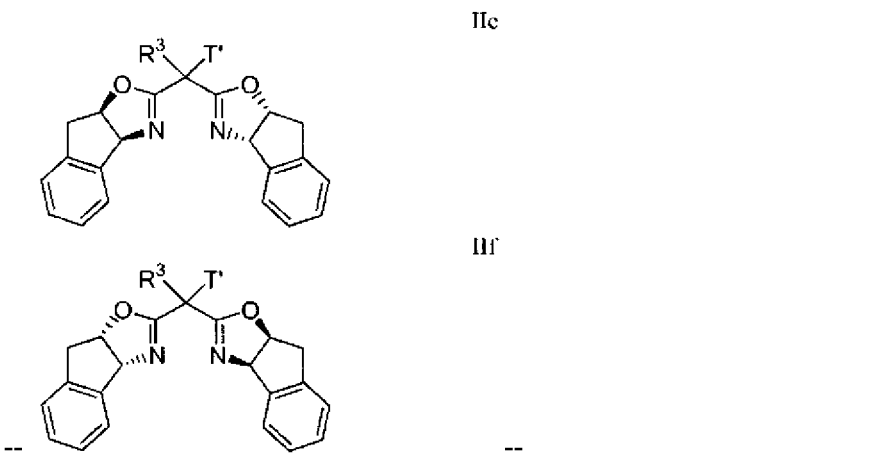
Column 5, line 33, "inorganic substrate" should be -- inorganic substrate. --
Column 7, lines 43-64, structures Ve and Vf should be
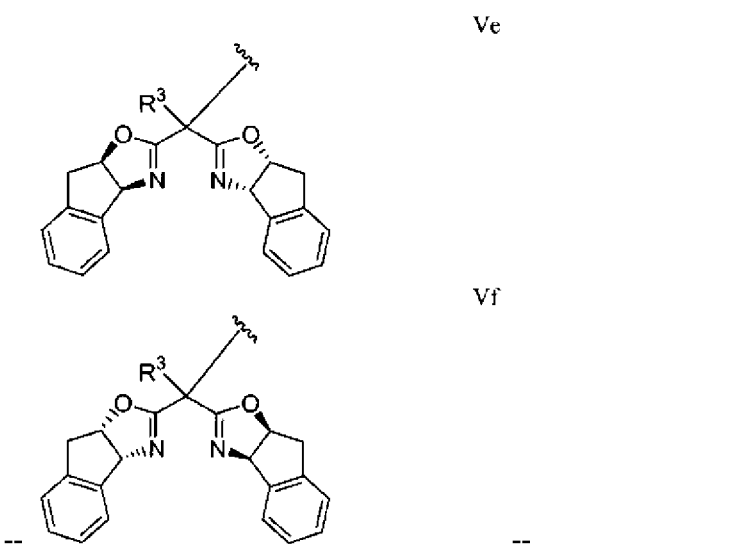
Column 9, line 13, "may an" should be -- may be an --
Column 9, line 35, "capable coupling" should be -- capable of coupling --
Column 9, line 44, "SiEt(O)Et)$_2$" should be -- SiEt(O)Et)$_2$. --
Claim 4, Column 15, lines 1-24, structures Ie and If should be

CERTIFICATE OF CORRECTION (continued)
U.S. Pat. No. 7,919,422 B2

Ie

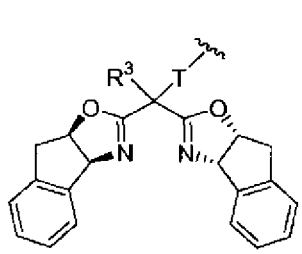

If

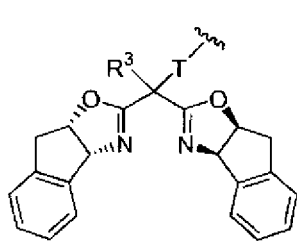

Claim 7, Column 16, lines 21-43, structures Ie and If should be

Ie

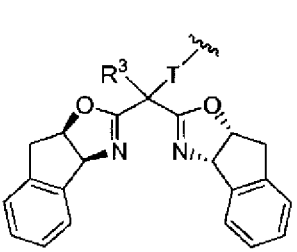

If

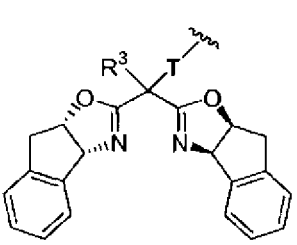

Claim 25, Column 18, lines 17-36, structures IIe and IIf should be

IIe

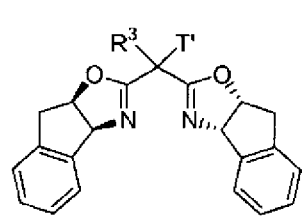

IIf

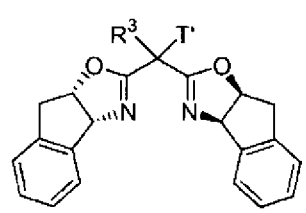

Claim 27, Column 19, line 51, "The process claim" should be -- The process of claim --

Claim 38, Column 19, line 38, "wherein the wherein the chiral" should be -- wherein the chiral --

UNITED STATES PATENT AND TRADEMARK OFFICE
CERTIFICATE OF CORRECTION

PATENT NO.         : 7,919,422 B2                                Page 1 of 3
APPLICATION NO.    : 11/885984
DATED              : April 5, 2011
INVENTOR(S)        : Jackie Y. Ying et al.

It is certified that error appears in the above-identified patent and that said Letters Patent is hereby corrected as shown below:

Column 2, lines 55-65, structure Ie should be

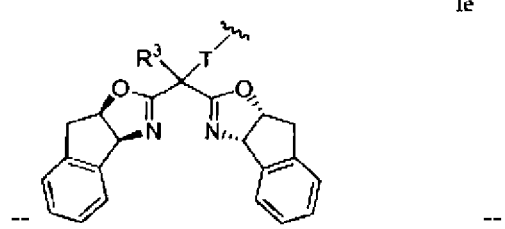

Column 3, lines 1-13, structure If should be

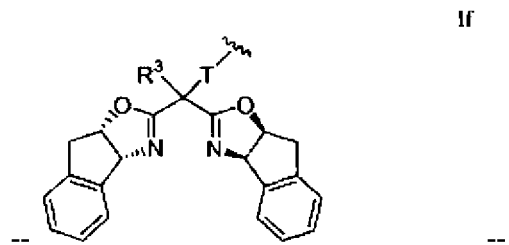

Column 3, line 23, "may an" should be -- may be an --

Column 3, line 24, "example" should be -- for example --

Column 3, lines 26 and 27, "arlylalkylene group" should be -- arylalkylene group -- both occurrences Column 4, line 19, "IIenry" should be -- Henry --

Column 4, line 37, "IIb, IIe, IId" should be -- IIb, IIc, IId --

This certificate supersedes the Certificates of Correction issued July 5, 2011 and August 23, 2011.

Signed and Sealed this
Eleventh Day of October, 2011

David J. Kappos
*Director of the United States Patent and Trademark Office*

Column 5, lines 10-28, structures IIe and IIf should be
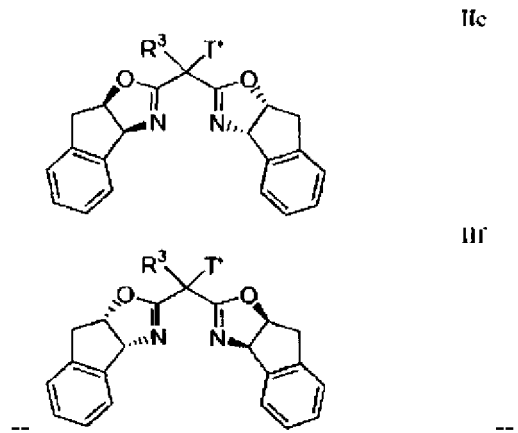
Column 5, line 33, "inorganic substrate" should be -- inorganic substrate. --
Column 7, lines 43-64, structures Ve and Vf should be
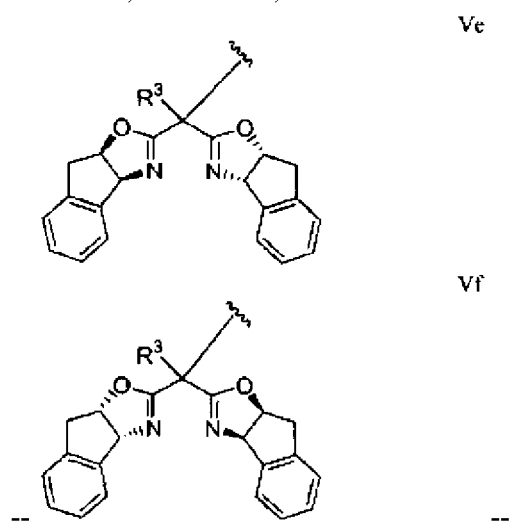
Column 9, line 13, "may an" should be -- may be an --
Column 9, line 35, "capable coupling" should be -- capable of coupling --
Column 9, line 44, "SiEt(OEt)$_2$" should be -- SiEt(OEt)$_2$. --
Claim 4, Column 15, lines 1-24, structures Ie and If should be

CERTIFICATE OF CORRECTION (continued)
U.S. Pat. No. 7,919,422 B2

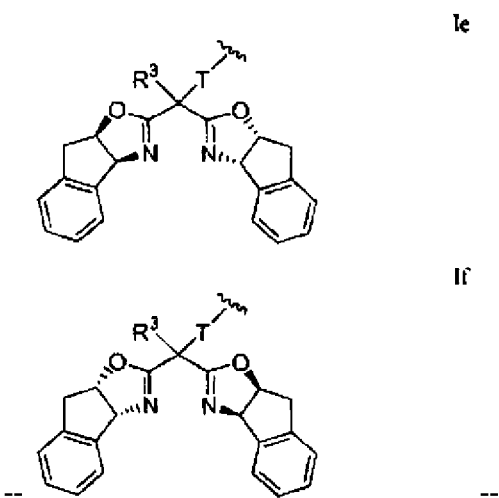

Claim 7, Column 16, lines 21-43, structures Ie and If should be

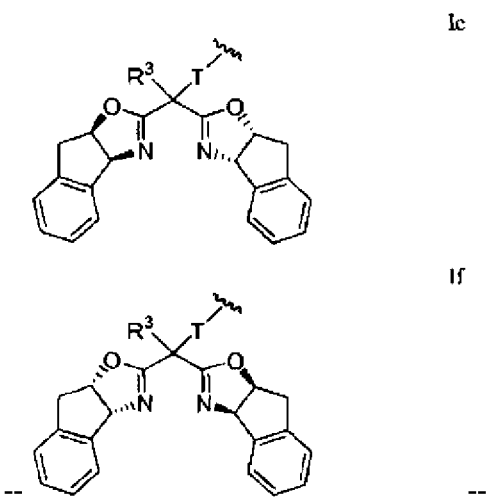

Claim 25, Column 18, lines 17-36, structures IIe and IIf should be

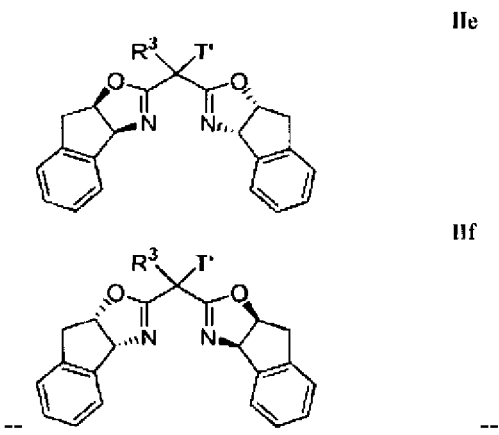

Claim 27, Column 19, line 51, "The process claim" should be -- The process of claim --

Claim 38, Column 19, line 38, "wherein the wherein the chiral" should be -- wherein the chiral --